(12) United States Patent
Baileykobayashi et al.

(10) Patent No.: US 12,285,476 B2
(45) Date of Patent: Apr. 29, 2025

(54) AMINO ACID SEQUENCE DERIVED FROM S PROTEIN OF SARS-CoV2 FOR GENERATING AN ANTI-SARS-CoV-2 ANTIBODY

(71) Applicant: TOAGOSEI CO., LTD., Tokyo (JP)

(72) Inventors: Nahoko Baileykobayashi, Tsukuba (JP); Tetsuhiko Yoshida, Tsukuba (JP)

(73) Assignee: TOAGOSEI CO., LTD., Tokyo (JP)

( * ) Notice: Subject to any disclaimer, the term of this patent is extended or adjusted under 35 U.S.C. 154(b) by 114 days.

(21) Appl. No.: 17/578,049

(22) Filed: Jan. 18, 2022

(65) Prior Publication Data

US 2022/0242916 A1    Aug. 4, 2022

(30) Foreign Application Priority Data

Jan. 29, 2021  (JP) ................................. 2021-012663

(51) Int. Cl.
*A61K 39/12* (2006.01)
*A61K 39/00* (2006.01)
*C07K 14/005* (2006.01)
*C07K 16/10* (2006.01)

(52) U.S. Cl.
CPC ............ *A61K 39/12* (2013.01); *C07K 14/005* (2013.01); *C07K 16/1003* (2023.08); *A61K 39/00* (2013.01); *C12N 2770/20022* (2013.01); *C12N 2770/20034* (2013.01)

(58) Field of Classification Search
CPC .... A61K 39/12; A61K 39/00; C07K 16/1003; C07K 14/005; C07K 16/10; C12N 2770/20022; C12N 2770/20034
See application file for complete search history.

(56) References Cited

U.S. PATENT DOCUMENTS

| | | | | |
|---|---|---|---|---|
| 7,491,793 | B2* | 2/2009 | Garry | C12N 7/00 |
| | | | | 530/300 |
| 10,787,501 | B1* | 9/2020 | Babb | A61K 39/395 |
| 11,241,493 | B2* | 2/2022 | Rauch | C12N 7/00 |
| 11,384,122 | B2* | 7/2022 | Langedijk | A61K 39/215 |
| 2021/0009718 | A1* | 1/2021 | Ambrogelly | C07K 14/475 |
| 2021/0379181 | A1* | 12/2021 | Rauch | A61K 47/6933 |
| 2023/0357328 | A1* | 11/2023 | Hikichi | A61K 39/215 |
| 2024/0067679 | A1* | 2/2024 | Kiyotani | A61P 31/14 |

FOREIGN PATENT DOCUMENTS

| | | | | | |
|---|---|---|---|---|---|
| CN | 111647054 | A  | * | 9/2020 | ........... C07K 14/005 |
| WO | 2017130716 | A1 | | 8/2017 | |
| WO | WO-2021188969 | A2 | * | 9/2021 | ........... A61K 39/215 |
| WO | WO-2022090752 | A1 | * | 5/2022 | ........... A61K 39/12 |

OTHER PUBLICATIONS

Li, W., Ran, Y., Li, M., Zhang, K., Qin, X., Xue, X., Zhang, C., Hao, Q., Zhang, W., & Zhang, Y. (2013). Mimotope vaccination for epitope-specific induction of anti-VEGF antibodies. BMC Biotechnology, 13(1), 77-77. (Year: 2013).*
Aguilar, A. et al. (2014). Study of Peptide Mimetics of Hepatitis A Virus Conjugated to Keyhole Limpet Hemocyanin and as Multiple Antigen Peptide System. International Journal of Peptide Research and Therapeutics, 20(1), 33-42. (Year: 2014).*
Wang, L., Fu, S., Cao, Y., Zhang, H., Feng, Y., Yang, W., Nie, K., Ma, X., & Liang, G. (2017). Discovery and genetic analysis of novel coronaviruses in least horseshoe bats in southwestern China. Emerging microbes & infections, 6(3), e14. (Year: 2017).*
Zhou, H. et al. (2020). A Novel Bat Coronavirus Closely Related to SARS-CoV-2 Contains Natural Insertions at the S1/S2 Cleavage Site of the Spike Protein. Current biology : CB, 30(11), 2196-2203. e3. (Year: 2020).*
Zhou, H. et al. (2020). Correction: A Novel Bat Coronavirus Closely Related to SARS-CoV-2 Contains Natural Insertions at the S1/S2 Cleavage Site of the Spike Protein. Current biology : CB, 30(19), 3896. (Year: 2020).*
Cokerton et al. GenBank Accession No. UYE28336.1. Direct Submission. Submitted Oct. 13, 2022. (Year: 2022).*
Garry and Wilson. GenBank Accession No. ACP58571.1. Seq ID No. 29 from U.S. Pat. No. 7,491,793. (Year: 2009).*
Langedijk et al. GenBank Accession No. WIU06475.1. Seq ID No. 210 from U.S. Pat. No. 11,384,122. (Year: 2020).*
Rauch et al. GenBank Accession No. WFJ29710.1. Seq ID No. 13,539 from U.S. Pat. No. 11,241,493. (Year: 2020).*
Zhao et al. CN 111647054 A. Machine Translation. (Year: 2020).*
Tohidinia, M., & Sefid, F. (2020). Identification B and T-Cell epitopes and functional exposed amino acids of S protein as a potential vaccine candidate against SARS-CoV-2/COVID-19. Microbial Pathogenesis, 148, 104459-104459. (Year: 2020).*
Li, Y. et al. (2020). Linear epitopes of SARS-CoV-2 spike protein elicit neutralizing antibodies in COVID-19 patients. Cellular & Molecular Immunology/Cellular & Molecular Immunology, 17(10), 1095-1097. (Year: 2020).*
Su, Wen, D., Yang, Q., Zhang, Y., Liu, C., & Wang, L. (2007). Comparison of phage pVIII and KLH as vector in inducing the production of cytokines in C57BL/6J mice. Vaccine, 25(6), 970-975. (Year: 2007).*
Wu, F., Zhao, S., Yu, B. et al. A new coronavirus associated with human respiratory disease in China. Nature 579, 265-269 (2020). https://doi.org/10.1038/s41586-020-2008-3.
Xia, S. Zhu, Y., Liu, M. et al. Fusion mechanism of 2019-nCoV and fusion inhibitors targeting HR1 domain in spike protein. Cell Mol Immunol 17, 765-767 (2020). https://doi.org/10.1038/s41423-020-0374-2.

* cited by examiner

*Primary Examiner* — Janet L Andres
*Assistant Examiner* — Carey Alexander Stuart
(74) *Attorney, Agent, or Firm* — Young Basile Hanlon & MacFarlane, P.C.

(57) ABSTRACT

The present disclosure provides a synthetic peptide containing an amino acid sequence that can be used to produce antibodies against proteins derived from a new coronavirus (SARS-CoV-2). The synthetic peptide provided herein is recognized as an antigen relative to at least one mammal, contains an amino acid sequence which is LNESLIDLQEL-GKYEQYIKWP (SEQ ID NO: 1), and has a total number of amino acid residues of 25 or less.

6 Claims, 1 Drawing Sheet

Specification includes a Sequence Listing.

AMINO ACID SEQUENCE DERIVED FROM S PROTEIN OF SARS-CoV2 FOR GENERATING AN ANTI-SARS-CoV-2 ANTIBODY

CROSS-REFERENCE TO RELATED APPLICATION(S)

This application claims priority to Japanese Application Patent Serial No. JP 2021-12663, filed Jan. 29, 2021, the entire disclosure of which is hereby incorporated by reference.

REFERENCE TO SEQUENCE LISTING SUBMITTED VIA EFS-WEB

This application includes an electronically submitted sequence listing in .txt format. The .txt file contains a sequence listing entitled "TOAGOSEI CO., LTD." created on Jan. 29, 2022, and is 544 bytes in size. The sequence listing contained in this .txt file is part of the specification and is hereby incorporated by reference herein in its entirety.

TECHNICAL FIELD

The present disclosure relates to novel synthetic peptides that can contribute to treatment of and prevention of the spread of infection with a new coronavirus (severe acute respiratory syndrome coronavirus 2; SARS-CoV-2) and use thereof.

BACKGROUND

SARS-CoV-2 is a virus that infects humans and causes coronavirus disease 2019 (CoVID-19) and is a pathogenic virus that rapidly causes symptoms such as severe pneumonia and sometimes kills infected persons. Since the discovery of an infectious disease due to this virus from December 2019 to early 2020, the infection has spread throughout the world and is a viral infectious disease that has a serious impact on the world economy and human life similarly to SARS, MERS, or the like well-known in the past.

A genome sequence of SARS-CoV-2 is disclosed in Wu, F., et al., Nature, Vol. 579, No. 7798 (2020), pp. 265-269 and can be viewed in the database disclosed by the National Center for Biotechnology Information (NCBI), for example. According to the database, it is predicted that there are at least 10 genes on the genome of SARS-CoV-2, and scientists in various fields such as virology, genetics, biochemistry, and pharmacy are rapidly conducting research thereon.

SUMMARY

However, in the present situation, no effective vaccine or antiviral agent for SARS-CoV-2 has been developed. For this reason, treatment of infected persons is limited to symptomatic treatment. Therefore, there is an urgent need to develop vaccines and antiviral agents for SARS-CoV-2. In addition, a plurality of SARS-CoV-2 variants have been confirmed, and there is a possibility that infection with various variants will spread in the future like influenza viruses. For this reason, in preparation for the spread of such infection, it is desirable to develop various vaccines and antiviral agents for SARS-CoV-2 and variants thereof.

Therefore, with the foregoing in view, it is a main object of the present disclosure to provide a synthetic peptide containing an amino acid sequence for producing an antibody against a protein derived from SARS-CoV-2. In addition, as another aspect, a further object thereof is to provide a composition containing the synthetic peptide. A further object thereof is to provide a method for producing an anti-SARS-CoV-2 antibody using the above-described synthetic peptide or composition.

The present inventors have conducted extensive studies, and as a result, have found that an antibody having a significantly high antibody titer can be obtained in a case where a peptide having a part of an amino acid sequence of a SARS-CoV-2-derived spike protein (hereinafter, also referred to as an "S protein") is used as an antigen. Such an amino acid sequence is a part of an S2 subunit associated with a function of fusing a cell membrane of a host cell and a viral envelope. Specifically, such an amino acid sequence is a part of heptad repeat 2 (HR2: 1163rd to 1213th amino acid residues) in the S2 subunit and is an amino acid sequence comprising a total of 21 (1193rd to $1213^{th}$) amino acid residues adjacent to a transmembrane region (1214th to 1237th amino acid residues) (refer to Xia, S., et al., Cellular & Molecular Immunology, Vol. 17 (2020), pp. 765-767).

That is, the synthetic peptide disclosed herein is a synthetic peptide recognized as an antigen relative to at least one mammal, in which the synthetic peptide contains an amino acid sequence below and a total number of amino acid residues is 25 or less.

LNESLIDLQELGKYEQYIKWP (SEQ ID NO: 1)

According to this, such a synthetic peptide has the amino acid sequence shown in SEQ ID NO: 1. Since the amino acid sequence is a part of the sequence of HR2 in the S protein derived from SARS-CoV-2, it is easily recognized as a foreign substance (antigen) exogenous to mammals. For this reason, mammals can produce antibodies having excellent antibody titers against such an amino acid sequence.

In addition, as another aspect, the composition disclosed herein is a composition containing a moiety recognized as an antigen relative to at least one mammal, the composition including: a synthetic peptide which contains an amino acid sequence shown in SEQ ID NO: 1 described above and in which a total number of amino acid residues is 25 or less; and a carrier protein.

According to such a configuration, the carrier protein is larger than the synthetic peptide in size and highly complicated. Therefore, it is possible to enhance immunogenicity.

In addition, in a preferred aspect of the composition disclosed herein, the above-described carrier protein is bound to the C-terminal side or the N-terminal side of the amino acid sequence constituting the above-described synthetic peptide through a predetermined cross-linking agent.

According to such a configuration, the synthetic peptide is in a state where it is farther apart from the surface of the carrier protein. Therefore, the probability that an antibody recognizing the above-described synthetic peptide will be produced can be improved.

In addition, the present disclosure provides a method for producing an anti-SARS-CoV-2 antibody in order to realize the above-described objects. That is, the method for producing an anti-SARS-CoV-2 antibody disclosed herein includes: using amino acid information shown in the above-described SEQ ID NO: 1 for an antigen for producing the antibody. Accordingly, it is possible to produce an antibody that recognizes an S protein derived from SARS-CoV-2.

DETAILED DESCRIPTION

Figure 1:
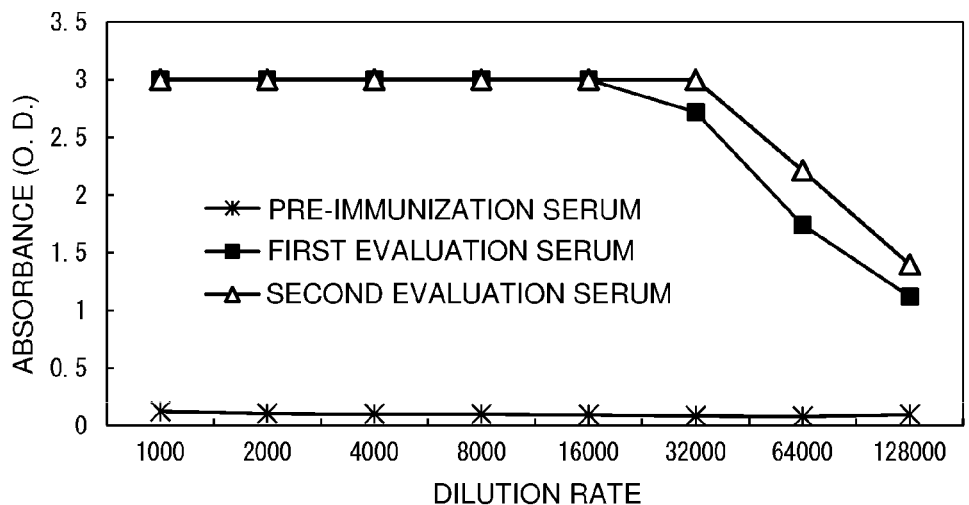
FIG. 1 is a graph in which antibody titers of a pre-immunization serum and first and second evaluation sera obtained in a step of administering a composition including keyhole limpet hemocyanin (KLH) and a synthetic peptide comprising an amino acid sequence of SEQ ID NO 1 to a first rabbit multiple times, against the synthetic peptide comprising an amino acid sequence of SEQ ID NO 1 are evaluated.

Hereinafter, a suitable embodiment of the present technology will be described. Matters (for example, general matters relating to chemical synthesis methods of peptides and preparation of compositions) other than those (for example, a primary structure or a chain length of a synthetic peptide disclosed herein) specifically mentioned in the present specification and necessary for the practice of the present technology can be understood by those skilled in the art as design matters based on techniques in the related art in the fields such as cell engineering, physiology, medicine, pharmacy, organic chemistry, biochemistry, genetic engineering, protein engineering, molecular biology, and genetics. The present technology can be implemented based on the contents disclosed in the present specification and common technical knowledge in the field. In the following description, depending on the situation, amino acids are represented by one-letter notation (but three-letter notation in the sequence listing) according to the nomenclature for amino acids shown in the IUPAC-IUB guidelines.

In addition, entire contents of all references cited in the present specification are incorporated in the present specification by reference.

The "synthetic peptide" in the present specification refers to peptide fragments of which peptide chains do not exist independently and stably in nature and which are artificially produced through chemical synthesis or biosynthesis (that is, production based on genetic engineering) and stably exist in a predetermined system (for example, a composition containing an adjuvant).

Here, the "peptide" is a term referring to an amino acid polymer having a plurality of peptide bonds and is not limited by the number of amino acid residues contained in peptide chains. However, the "peptide" referred to herein typically has a relatively small molecular weight as the total number of amino acid residues is substantially 100 or less (preferably 80 or less and more preferably 70 or less, for example, 60 or less).

In addition, unless otherwise specified, the "amino acid residues" in the present specification is a term including an N-terminal amino acid and a C-terminal amino acid of a peptide chain.

In addition, a "conjugate" in the present specification is a product formed by binding a carrier protein and other components (for example, a cross-linking agent, a Cys residue, and a spacer) to the above-described synthetic peptide and is included in the composition disclosed herein.

In the amino acid sequences described in the present specification, the N-terminus is always on the left side and the C-terminus is always on the right side.

The synthetic peptide disclosed herein contains a part of an amino acid sequence of an S protein encoded by a genome of SARS-CoV-2 disclosed in the public international organization databases (for example, National Center for Biotechnology Information: NCBI). That is, the synthetic peptide contains the following amino acid sequence:

LNESLIDLQELGKYEQYIKWP (SEQ ID NO: 1). Typically, the synthetic peptide disclosed herein comprises only the amino acid sequence shown in SEQ ID NO: 1. In addition, as long as a part of the amino acid sequence shown in SEQ ID NO: 1 is an epitope, the synthetic peptide may include a modified sequence of the amino acid sequence. Here, the "modified sequence" is an amino acid sequence (modified amino acid sequence) formed by substitution, deletion, and/or addition (insertion) of one or several (typically two or three) amino acid residues. Since such a minor modified sequence can be easily used by those skilled in the art based on the information disclosed herein, it is included in the "synthetic peptide" as a technical idea disclosed herein.

The amino acid sequence of SEQ ID NO: 1 is an amino acid sequence comprising a total of 21 1193rd to 1213th amino acid residues of a SARS-CoV-2-derived S protein (also registered as "surface glycoprotein" on NCBI. Such an amino acid sequence is a part of HR2 (1163rd to 1213th amino acid sequence) in the S2 subunit contained in the S protein and is adjacent to a transmembrane region (1214th to 1237th amino acid sequence). That is, the amino acid sequence shown in SEQ ID NO: 1 is a site exposed outside a viral envelope. For this reason, an antibody having such an amino acid sequence as an epitope can recognize an S protein contained in naturally existing SARS-CoV-2.

In addition, the synthetic peptide disclosed herein may contain an amino acid sequence other than the amino acid sequence shown in SEQ ID NO: 1 as long as it is recognized as an antigen relative to at least one mammal. Although not particularly limited, for example, the 1192nd amino acid residue of an S protein of SARS-CoV-2 may be continuous with the N-terminal side of the amino acid sequence shown in SEQ ID NO: 1, or 1191st, 1190th, and 1189th amino acid residues may be further added thereto in this order. The amino acid sequence to which these amino acid residues are added to the N-terminal side is a part of an amino acid sequence of a naturally existing S protein. For this reason, an antibody having such an amino acid sequence as an epitope can recognize a naturally existing S protein. These amino acid residues can be confirmed in the database of S protein amino acid sequences disclosed in the public international organization databases (for example, NCBI).

In addition, it is preferable that a Cys residue be added to the N-terminal or C-terminal side of the amino acid sequence of the synthetic peptide disclosed herein. Since no Cys residue is contained in the amino acid sequence shown in SEQ ID NO: 1, no thiol group (SH group) is contained therein. For this reason, a thiol group (SH group) can be selectively added to the amino acid sequence shown in SEQ ID NO: 1 by adding a Cys residue thereto. Accordingly, since it is possible to selectively cause a reaction between a thiol group and maleimide, it is possible to bind a cross-linking agent containing maleimide thereto at a desired position, for example.

The total number of amino acid residues in the synthetic peptide disclosed herein is suitably 25 or less. In a case where the total number of amino acid residues therein is larger than that, an antibody having one other than the amino acid sequence shown in SEQ ID No NO: 1 as an epitope is likely produced when the synthetic peptide is administered to organisms such as mammals. In addition, from the viewpoint of limiting the site to being an epitope, the total number of amino acid residues may be 24 or less, 23 or less, 22 or less, or 21.

In addition, an N-terminal amino group of the synthetic peptide disclosed herein may be N-acetylated. When an N-terminal amino acid residue is N-acetylated, solubility of a synthetic peptide can be improved.

The synthetic peptide disclosed herein can be easily produced according to a usual chemical synthesis method. For example, either a solid-phase synthesis method or a liquid-phase synthesis method well-known in the related art may be employed. A solid-phase synthesis method in which a t-butyloxycarbonyl (Boc) group or a 9-fluorenylmethoxycarbonyl (Fmoc) group is applied as a protecting group for an amino group is suitable.

Alternatively, a synthetic peptide may be biosynthesized based on a genetic engineering technique. That is, a polynucleotide (typically DNA) of a nucleotide sequence (containing an ATG start codon) encoding an amino acid sequence of a desired synthetic peptide is synthesized. A recombinant vector having an expression gene construct comprising the synthesized polynucleotide (DNA) and various regulatory elements (including a promoter, a ribosome binding site, a terminator, an enhancer, and various cis-elements controlling an expression level) for expressing the amino acid sequence in host cells is constructed depending on the host cells.

This recombinant vector is introduced into predetermined host cells (for example, yeast, insect cells, or plant cells) through an ordinary technique to culture the host cells, or tissue or an individual containing the cells under predetermined conditions. As a result, a target peptide can be expressed and produced in the cells. Then, the peptide can be isolated from the host cells (or from a culture medium in a case of being secreted therein), and refolding or purification can be performed as necessary to obtain a target synthetic peptide.

Since a method carried out in the related art in the field may be employed as it is as the method for constructing a recombinant vector and the method for introducing a constructed recombinant vector into host cells and such methods themselves do not particularly characterize the present technology, detailed explanation thereof will be omitted.

Alternatively, a target polypeptide can be synthesized in vitro by employing a so-called cell-free protein synthesis system by constructing template DNA for the cell-free protein synthesis system (that is, a synthetic gene fragment containing a nucleotide sequence that encodes an amino acid sequence of a synthetic peptide) and using various compounds (such as ATP, RNA polymerase, and amino acids) required for peptide synthesis. Regarding the cell-free protein synthesis system, a paper of Shimizu, et al. (Shimizu, et al., Nature Biotechnology, 19, 751-755 (2001)) and a paper of Madin et al. (Madin, et al., Proc. Natl. Acad. Sci., USA, 97(2), 559-564 (2000)) can be referred to, for example. Many private companies have already undertaken contract production of polypeptides based on the techniques described in these papers at the time of filing the present application, and cell-free protein synthesis kits are available commercially (for example, available from CellFree Sciences Co., Ltd. in Japan).

A nucleotide sequence encoding the synthetic peptide disclosed herein and/or a single-stranded or double-stranded polynucleotide containing a nucleotide sequence complementary to the nucleotide sequence encoding the synthetic peptide can be easily produced (synthesized) according to a well-known conventional method. That is, a codon corresponding to each amino acid residue constituting a designed amino acid sequence is selected to easily determine and provide a nucleotide sequence corresponding to the amino acid sequence of the synthetic peptide. Once the nucleotide sequence is determined, a (single-stranded) polynucleotide corresponding to the desired nucleotide sequence can be easily obtained using a DNA synthesizer or the like. Target double-stranded DNA can be further obtained by using the obtained single-stranded DNA as a template and employing various enzymatic synthesis means (typically, polymerase chain reaction: PCR). In addition, the polynucleotide may be in a form of DNA or in a form of RNA (mRNA or the like). DNA can be provided as a double strand or a single strand. In the case where DNA is provided as a single strand, the strand may be a coding strand (sense strand) or non-coding strand (antisense strand) of a sequence complementary thereto.

The polynucleotide obtained in this manner can be used as a material for constructing a recombinant gene (expression cassette) for producing a synthetic peptide in various host cells or with a cell-free protein synthesis system as described above.

The synthetic peptide disclosed herein is recognized as an antigen relative to at least one mammal and can promote production of antibodies (such as IgM and IgG) that recognize the synthetic peptide. The synthetic peptide may be in the form of a salt as long as it is recognized as an antigen relative to at least one mammal. For example, an acid addition salt of the peptide that can be obtained through an addition reaction of an ordinarily used inorganic acid or organic acid can be used according to a usual method. Alternatively, the synthetic peptide may be another salt (for example, a metal salt) as long as it is recognized as an antigen relative to at least one mammal. The "peptide" mentioned in the present specification and claims includes such a salt form.

The synthetic peptide disclosed herein is also provided as a part of a composition containing a carrier protein. That is, the composition disclosed herein is a composition containing a moiety recognized as an antigen relative to at least one mammal, the composition including: a synthetic peptide which contains an amino acid sequence: LNESLIDLQEL-GKYEQYIKWP (SEQ ID NO: 1), and in which a total number of amino acid residues is 25 or less; and a carrier protein.

The type of carrier protein is not particularly limited, but all of keyhole limpet hemocyanin (KLH), ovalbumin (OVA), bovine serum albumin (BSA), and the like having an antigenic stimulation can be suitably used, for example.

In the composition disclosed herein, a carrier protein is preferably bound to the C-terminal side or the N-terminal side of the above-described synthetic peptide through a predetermined cross-linking agent.

As a cross-linking agent, one having a heterobifunctional group or a homobifunctional group usually used for cross-linking a peptide can be used. Examples of common functional groups of cross-linking agents include N-hydroxysuccinimide-activated esters (NHS esters), maleimide, azide, and iodoacetamide. In addition, examples of preferred reactive functional groups that react with the functional groups of such cross-linking agents include various amine-containing compounds (for example, primary amines), thio-containing or other sulfur-containing groups, carboxyl, and hydroxyl. The above-described NHS esters can efficiently react with amines at neutral or higher pH to form a significantly stable amide bond. In addition, the above-described maleimide has an SH group-selective reaction and has excellent reactivity with SH groups in neutral conditions compared to amines.

Examples of suitable cross-linking agents having a homobifunctional group include N-hydroxysuccinimide (NHS), disuccinimidyl suberate (DSS), bis(sulfosuccinimidyl) suberate ($BS^3$), dithiobis(succinimidyl propionate) (DSP), dithiobis(sulfosuccinimidyl propionate) (DTSSP), ethylene glycol bis(succinimidyl succinate) (EGS), ethylene glycol bis (sulfosuccinimidyl succinate) (sulfo-EGS), disuccinimidyl tartrate (DST), and disulfosuccinimidyl tartrate (sulfo-DST). In particular, bis(sulfosuccinimidyl) suberate ($BS^3$) can be preferably used.

In addition, as preferred cross-linking agents having a heterobifunctional group, derivatives of ethylene glycol (PEG) such as O—[N-(3-maleimidepropionyl)aminoethyl]-O'-[3-(N-succinimidyloxy)-3-oxopropyl]heptacosane ethylene glycol, N-(6-maleimidecaproyloxy) succinimide (EMCS), m-maleimide benzoyl-N-hydroxysuccinimide ester (MBS), succinimidyl 4-[maleimidophenyl]butyrate (SMPB), succinimidyl 4-(maleimidomethyl)cyclohexane-1-carboxylate (SMCC), N-(γ-maleimidebutyroxy) succinimide ester (GMBS), m-maleimide propionic acid-N-hydroxysuccinimide ester (MPS), and N-succinimidyl (4-iodoacetyl)aminobenzoate (SIAB) can be preferably used. In particular, EMCS or a PEG derivative having an NHS ester and maleimide as reactive functional groups can be preferably used.

Although the position at which a synthetic peptide binds to a cross-linking agent is not particularly limited, the N-terminal side or the C-terminal side is preferable. Accordingly, the synthetic peptide is in a state where it is farther apart from the surface of the carrier protein. Therefore, the probability that an antibody recognizing the synthetic peptide will be produced is improved. For example, a composition in which a cross-linking agent having maleimide is added to an amino acid sequence where a Cys residue is present on the N-terminal side or the C-terminal side can be suitably used.

PEG has a property of showing little immunogenicity in addition to improving solubility in water and human body fluids. Furthermore, PEG has a property of hardly decomposing in fluids in the human body. For this reason, PEG can be suitably used not only as a cross-linking agent but also as a spacer for improving the solubility of a synthetic peptide. A method for introducing PEG as a spacer may be the same as that for introducing the above-described cross-linking agent. In addition, the method may be the same as the synthetic peptide production method according to the above-described usual chemical synthesis methods. For example, by using PEG having an amino group having a carboxyl group at one end and a protective group (for example, Boc or Fmoc) at the other end, the PEG can be treated in the same manner as a usual amino acid. Therefore, the PEG can be introduced as a spacer into an amino acid sequence at a desired position through a solid-phase synthesis method, for example. Accordingly, it is possible to, for example, bind a Cys residue to the carboxyl group side of the PEG as a spacer and to prepare a composition in which PEG, a cross-linking agent, and a carrier protein are bound to a synthetic peptide by binding the Cys residue to the cross-linking agent bound to the carrier protein.

Regarding the length of PEG, those used for a spacer or a cross-linking agent in the related art may be used. For example, lengths in which 2 to 24 PEG units ($-CH_2-CH_2-O-$) are repeated can be used.

The synthetic peptide or the composition containing the amino acid sequence represented by SEQ ID NO: 1 disclosed herein can be used for producing anti-SARS-CoV-2 antibodies. Since the synthetic peptide and the composition containing the amino acid sequence represented by SEQ ID NO: 1 are highly antigenic to mammals, these can be used for producing antibodies having higher antibody titers.

An example of a typical method of using them is a vaccine. The above-described synthetic peptide and composition can be used for vaccination against SARS-CoV-2 or in a therapeutic agent for SARS-CoV-2. In addition, other typical examples include administration of the above-described synthetic peptide and composition as antigens to organisms such as mammals to produce antibodies recognizing the synthetic peptide.

As mammals to be immunized, experimental animals such as guinea pigs, rats, mice, rabbits, and sheep are used. Rats, mice, and rabbits are suitable to obtain monoclonal antibodies or polyclonal antibodies. Any administration routes such as subcutaneous, intraperitoneal, intravenous, intramuscular, and intradermal routes may be used as the immunization method, and it is mainly preferable to perform injection subcutaneously, intradermally, intraperitoneally, or intravenously. In addition, various methods can be used without particular limitation on the immunity interval, immunizing dose, or the like. For example, a method for performing immunization about 2 to 10 times at 2-week intervals to collect specimens from a living body about 1 to 5 times, preferably after about 2 to 7 days from the final immunization is often used. In addition, the immunizing dose does not limit the amount of peptide to be administered at one time, but about 50 µg to 300 µg thereof per one rabbit is preferably used, for example. In addition, although not particularly limited, at the first time, a conjugate containing a synthetic peptide and a carrier protein is well mixed with an adjuvant (for example, Freund's complete adjuvant (FCA)), the mixture is administered intraperitoneally to a mouse, and cells are made to proliferate. The conjugate is well mixed with an adjuvant (for example, FCA or Freund's incomplete adjuvant (FIA)) again at 2-week intervals, the mixture is intraperitoneally administered, and, by collecting via ascites monoclonal antibodies or polyclonal antibodies having higher antibody titers against the above-described synthetic peptide can be efficiently obtained. Purification of target monoclonal antibodies or polyclonal antibodies can be performed through a well-known method such as affinity chromatography, ion exchange chromatography, a gel filtration method, or ammonium sulfate fractionation.

The synthetic peptide and composition disclosed herein may include a variety of pharmaceutically acceptable carriers depending on use forms if the synthetic peptide is recognized as an antigen relative to at least one mammal. For example, carriers commonly used in peptide-based pharmaceuticals can be suitably applied as diluents, excipients, and the like.

Although the carriers may appropriately vary depending on the applications or forms of the synthetic peptide and the composition containing the above-described carriers, typical examples of the above-described carriers include water, a physiological buffer solution, and various organic solvents. In addition, an aqueous alcohol (such as ethanol) solution at an appropriate concentration, glycerol, and non-drying oils such as olive oil can be used. Alternatively, a liposome may be used. In addition, examples of secondary components that can be contained in the above-described composition include various fillers, extenders, binders, humectants, surfactants, pigments, fragrances, and adjuvants.

Examples of typical forms of the synthetic peptide and the composition containing the above-described carriers include a liquid medicine, suspensions, emulsions, aerosols, foaming agents, granules, powdery agents, tablets, capsules, ointments and aqueous gel. In addition, the forms thereof may be freeze-dried products or granulated products for preparing a drug solution by dissolving the synthetic peptide and the composition in physiological saline or a suitable buffer solution (for example, PBS) immediately before use in order to use the synthetic peptide and the composition for injection or the like.

Since the process itself for preparing various forms of compositions (medicines) using the synthetic peptide (main component) and various carriers (secondary components) as materials may be based on a well-known conventional method and such a production method itself does not characterize the present technology, detailed description thereof will be omitted. Examples of a detailed source of information on the formulations include Comprehensive Medicinal Chemistry, supervised by Corwin Hansch, published by Pergamon Press (1990). The entire contents of this publication are incorporated in the present specification by reference.

Hereinafter, several test examples of the present technology will be described, but the present technology is not intended to be limited to those shown in such test examples.

Synthesis of Peptide

A PEG-containing synthetic peptide including a peptide comprising an amino acid sequence shown in SEQ ID NO: 1, PEG bound as a spacer to the C-terminus of the peptide, and a Cys residue bound to the PEG was produced using a commercially available peptide synthesizer. That is, similarly to a usual amino acid sequence, synthesis was performed so as to obtain the following sequence in which the N-terminus was on the left side and the C-terminus was on the right side.
(Synthetic Peptide Comprising SEQ ID NO: 1)-(PEG)-(Cys Residue)

Such synthesis was carried out through a solid-phase synthesis method (Fmoc method) according to the manual of the peptide synthesizer. Since the mode of use of the peptide synthesizer itself does not characterize the present technology, detailed description will be omitted. In addition, PEG 8 in which a PEG unit is repeated 8 times was used as PEG.

Production of Conjugate Using Peptide

Keyhole limpet hemocyanin (KLH) which is a carrier protein was bound to the obtained PEG-containing synthetic peptide using N-(6-maleimidecaproyloxy) succinimide (EMCS) which is a cross-linking agent to produce a conjugate. Since the reaction itself for binding these does not characterize the present technology, detailed description thereof will be omitted. For brief description, first, when an amino group in KLH is allowed to react with an NHS ester in EMCS, EMCS is bound to the surface of KLH. Thereafter, by reacting maleimide in such EMCS with a thiol group of a Cys residue present on the C-terminal side of the above-described PEG-containing synthetic peptide and binding these, a conjugate obtained by binding the above-described PEG-containing synthetic peptide to KLH through a cross-linking agent was produced.

Antibody Production Using Conjugate as Antigen

The obtained conjugate was administered to two Japanese white rabbits (hereinafter, also referred to as a first rabbit and a second rabbit when distinguishing individual rabbits) to produce antibodies against the above-described synthetic peptide. In addition, blood was collected from the above-described rabbits as appropriate to evaluate antibody titers to be described below. Specifically, 5 mL trial blood collection was performed before administering the conjugate on day 1 (hereinafter, the number of days based on this day will be referred to) to prepare pre-immunization sera. In addition, on the same day, a composition obtained by mixing 0.15 mg of the above-described conjugate with an equal amount of FCA was intradermally administered (first intradermal administration) to the above-described rabbits. On day 15, a composition obtained by mixing 0.3 mg of the above-described conjugate with an equal amount of FCA was intradermally administered (second intradermal administration) to the above-described rabbits. On day 29, a composition obtained by mixing 0.3 mg of the above-described conjugate with an equal amount of FCA was intradermally administered (third intradermal administration) to the above-described rabbits. On day 36, 5 mL trial blood collection was performed from the above-described rabbits to prepare first evaluation sera. On day 43, a composition obtained by mixing 0.3 mg of the above-described conjugate with an equal amount of FCA was intradermally administered (fourth intradermal administration) to the above-described rabbits. On day 50, 5 mL trial blood collection was performed from the above-described rabbits to prepare second evaluation sera. Sodium azide was added to the prepared pre-immunization sera and first and second evaluation sera during preparation so that the content thereof became 0.09%, and the mixtures were preserved.

Evaluation of Antibody Titers of Sera

Antibody titers of the pre-immunization sera and the first and second evaluation sera were evaluated through an enzyme-linked immunosorbent assay (ELISA) method.

Figure 2:
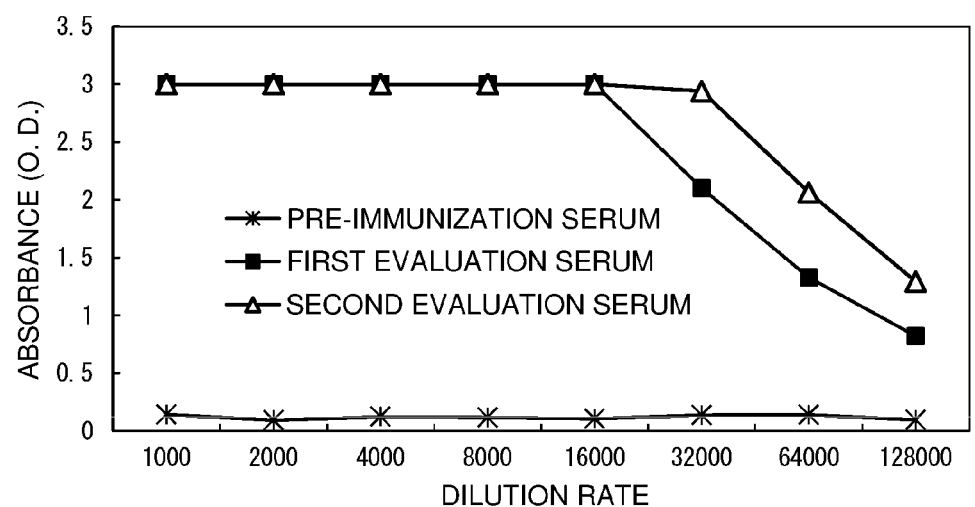
FIG. 2 is a graph in which antibody titers of a pre-immunization serum and first and second evaluation sera obtained in a step of administering a composition including keyhole limpet hemocyanin (KLH) and a synthetic peptide comprising an amino acid sequence of SEQ ID NO 1 to a second rabbit multiple times, against the synthetic peptide comprising an amino acid sequence of SEQ ID NO 1 are evaluated.

First, the above-described synthesized synthetic peptide was dissolved in phosphate-buffered saline (PBS) having a pH of 7.2 so as to have a concentration of 5 µg/mL, and 100 µg of the mixture was added to each well of a microplate (manufactured by Nalge Nunc, cat #442404, flat-bottomed 96 wells) to perform incubation for 2 hours at room temperature. Next, the liquid in each well was removed and then washed three times with PBS (washing liquid) containing 0.2% Tween-20 (polyoxyethylene (20) sorbitan monolaurate, manufactured by FUJIFILM Wako Pure Chemical Corporation). Thereafter, the washing liquid was added to each well and incubated overnight at 4° C. After incubation, the pre-immunization sera and the first and second evaluation sera were respectively diluted by 1000 times, 2000 times, 4000 times, 8000 times, 16000 times, 32000 times, 64000 times, and 128000 times using PBS (diluted solution)

containing 0.05% Tween-20, the above-described washing liquid of each well was removed, and 100 μL of each diluted solution was added to separate wells, incubated at 37° C. for 30 minutes, and then further incubated at room temperature for 15 minutes. The liquid in each well was removed and then washed three times with the above-described washing liquid, and 100 μL of a diluted solution obtained by diluting goat f(ab)'2 anti rabbit IgG's HRP conjugate (manufactured by MP Biomedicals, LLC-Cappel Products) 5000 times with the above-described diluted solution was added to each well, incubated at 37° C. for 30 minutes, and then further incubated at room temperature for 15 minutes. The liquid in each well was removed and then washed three times with the above-described washing liquid, and 100 μL of a substrate solution obtained by dissolving 10 mg of O-phenylene diamin (OPD, manufactured by SIGMA-Aldrich) in 25 mL of a citrate-phosphate buffer solution and adding 5 μL of hydrogen peroxide thereto was added to each well. Thereafter, color development was performed at room temperature for 20 minutes and stopped by adding 100 μL of 1 M sulfuric acid to each well. Then, the absorbance of each well at 490 nm was measured with an Immuno Reader. The results are shown in FIGS. 1 and 2. As an evaluation criterion, in a case where the absorbance at 490 nm is 0.5 or more, an antibody has a guaranteed antibody titer. In addition, in a case where the above-described absorbance exceeds the measurement upper limit of the Immuno Reader (in a case where the above-described absorbance exceeds 3.0), the absorbance is indicated as 3.0.

As shown in FIGS. 1 and 2, in both of the first and second rabbits, the first and second evaluation sera showed absorbances higher than 0.5 at any dilution rate. In addition, even if the dilution rate was 16000 times, the sera showed high absorbances exceeding the measurement upper limit of the Immuno Reader. From these results, it can be seen that, when a composition containing a synthetic peptide comprising SEQ ID NO: 1 is used, an antibody having an excellent antibody titer against such a synthetic peptide can be obtained.

Specific examples of the present technology are shown in detail in the preceding, but these are nothing more than examples and do not limit the scope of the claims. Various and diverse modifications and alterations to the specific examples provided above as examples are included in the art described in the claims.

As described above, when the synthetic peptide and the composition (for example, a conjugate) disclosed herein are administered to mammals, antibodies which have high antibody titers and recognize the synthetic peptide can be produced in the mammals. For this reason, the synthetic peptide and the composition provided by the present disclosure can be used as vaccines against SARS-CoV-2. In addition, produced antibodies can be antiviral agents against SARS-CoV-2. Furthermore, produced antibodies can also be used for SARS-CoV-2 detection, labeling, or the like.

What is claimed is:

1. An artificial synthetic peptide recognized as an antigen relative to at least one mammal, wherein
the artificial synthetic peptide consists of an amino acid sequence: LNESLIDLQELGKYEQYIKWP (SEQ ID NO: 1) and the N-terminal amino group of the artificial synthetic peptide is an N-acetylated amino group.

2. A composition that contains a moiety recognized as an antigen relative to at least one mammal, the composition comprising:
an artificial synthetic peptide consisting of an amino acid sequence: LNESLIDLQELGKYEQYIKWP (SEQ ID NO: 1); and
a carrier protein, wherein the N-terminal amino group of the artificial synthetic peptide is an N-acetylated amino group and the carrier protein is bound to the C-terminal side or the N-terminal side of the amino acid sequence constituting the artificial synthetic peptide through a cross-linking agent.

3. A method for producing an anti-severe acute respiratory syndrome coronavirus 2 (anti-SARS-CoV-2) antibody, the method comprising:
preparing a composition comprising an artificial synthetic peptide consisting of an amino acid sequence: LNESLIDLQELGKYEQYIKWP (SEQ ID NO: 1) and a carrier protein, wherein the N-terminal amino group of the artificial synthetic peptide is an N-acetylated amino group and the carrier protein is bound to the C-terminal side or the N-terminal side of the amino acid sequence of the artificial synthetic peptide through a cross-linking agent; and
administering the composition to a subject to produce the antibody against the peptide.

4. The method according to claim 3, wherein the subject is a mammal.

5. The composition according to claim 2, wherein the carrier protein is keyhole limpet hemocyanin (KLH), ovalbumin (OVA), or bovine serum albumin (BSA).

6. The method according to claim 3, wherein the carrier protein is keyhole limpet hemocyanin (KLH), ovalbumin (OVA), or bovine serum albumin (BSA).

* * * * *

SEQUENCE LISTING

```
<160> NUMBER OF SEQ ID NOS: 1

<210> SEQ ID NO 1
<211> LENGTH: 21
<212> TYPE: PRT
<213> ORGANISM: Artificial Sequence
<220> FEATURE:
<223> OTHER INFORMATION: Synthetic peptide

<400> SEQUENCE: 1

Leu Asn Glu Ser Leu Ile Asp Leu Gln Glu Leu Gly Lys Tyr Glu Gln
1               5                   10                  15

Tyr Ile Lys Trp Pro
            20
```